US009963509B2

(12) United States Patent
DuBridge et al.

(10) Patent No.: US 9,963,509 B2
(45) Date of Patent: May 8, 2018

(54) ANTI-B7H3 BINDING COMPOUNDS AND USES THEREOF

(71) Applicant: Full Spectrum Genetics, Inc., Belmont, CA (US)

(72) Inventors: Robert DuBridge, Belmont, CA (US); Veronica Juan, Redwood City, CA (US)

(73) Assignee: Full Spectrum Genetics, Inc., Belmont, CA (US)

( * ) Notice: Subject to any disclaimer, the term of this patent is extended or adjusted under 35 U.S.C. 154(b) by 0 days. days.

(21) Appl. No.: 15/525,898

(22) PCT Filed: Dec. 14, 2015

(86) PCT No.: PCT/US2015/065645
§ 371 (c)(1),
(2) Date: May 10, 2017

(87) PCT Pub. No.: WO2016/106004
PCT Pub. Date: Jun. 30, 2016

(65) Prior Publication Data
US 2017/0362322 A1    Dec. 21, 2017

Related U.S. Application Data

(60) Provisional application No. 62/095,969, filed on Dec. 23, 2014, provisional application No. 62/105,135, filed on Jan. 19, 2015.

(51) Int. Cl.
*A61K 39/00* (2006.01)
*C07K 16/28* (2006.01)
*C07K 16/30* (2006.01)

(52) U.S. Cl.
CPC .......... *C07K 16/2827* (2013.01); *C07K 16/30* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| 7,462,607 | B2 | 12/2008 | Cheung |
| 7,507,724 | B2 | 3/2009 | Cheung |
| 7,666,424 | B2 | 2/2010 | Cheung et al. |
| 7,737,258 | B2 | 6/2010 | Cheung |
| 7,740,845 | B2 | 6/2010 | Cheung |
| 8,148,154 | B2 | 4/2012 | Cheung et al. |
| 8,414,892 | B2 | 4/2013 | Cheung |
| 8,501,471 | B2 | 8/2013 | Cheung |
| 8,633,170 | B2 | 1/2014 | Cheung |
| 8,791,252 | B2 | 7/2014 | Cheung |
| 9,062,110 | B2 | 6/2015 | Cheung |
| 9,315,585 | B2 | 4/2016 | Cheung et al. |
| 9,480,700 | B2 | 11/2016 | Cheung |
| 9,688,772 | B2 | 6/2017 | Cheung et al. |
| 2002/0102264 | A1 | 8/2002 | Cheung |
| 2003/0103963 | A1 | 6/2003 | Cheung |
| 2003/0147881 | A1 | 8/2003 | Cheung et al. |
| 2004/0116379 | A1 | 6/2004 | Cheung |
| 2005/0169932 | A1 | 8/2005 | Cheung |
| 2006/0020128 | A1 | 1/2006 | Cheung |
| 2006/0051359 | A1 | 3/2006 | Pastan et al. |
| 2008/0193456 | A1 | 8/2008 | Cheung |
| 2010/0143245 | A1 | 6/2010 | Cheung |
| 2010/0226914 | A1 | 9/2010 | Cheung et al. |
| 2010/0284920 | A1 | 11/2010 | Cheung |
| 2010/0310571 | A1 | 12/2010 | Cheung |
| 2011/0195071 | A1 | 8/2011 | Cheung |
| 2013/0216528 | A1 | 8/2013 | Cheung et al. |
| 2013/0230535 | A1 | 9/2013 | Cheung |
| 2013/0287798 | A1 | 10/2013 | Cheung |
| 2014/0161814 | A1 | 6/2014 | Cheung |
| 2014/0335100 | A1 | 11/2014 | Cheung |
| 2016/0176981 | A1 | 6/2016 | Cheung et al. |
| 2017/0129964 | A1 | 5/2017 | Cheung |
| 2017/0232099 | A1 | 8/2017 | Cheung |
| 2017/0240637 | A1* | 8/2017 | Cheung .............. C07K 16/2827 |
| 2017/0253660 | A1 | 9/2017 | Cheung et al. |

FOREIGN PATENT DOCUMENTS

| WO | WO/2002/032375 | 4/2002 |
| WO | WO/2002/058711 | 8/2002 |
| WO | WO/2003/033670 | 4/2003 |
| WO | WO/2003/075846 | 9/2003 |
| WO | WO2004/050849 | 6/2004 |
| WO | WO2008/116219 | 9/2008 |
| WO | WO 2008116219 | * 9/2008 |
| WO | WO/2011/160119 | 12/2011 |
| WO | WO2014/138306 | 9/2014 |

(Continued)

OTHER PUBLICATIONS

Kramer et al, "Compartmental intrathecal radioimmunotherapy: results for treatment for metastatic CNS neuroblastoma," J. Neurooncol., 97(3): 409-418 (2010).
Loo et al, "B7-H3 and its role in antitumor immunity," Clinical and Developmental Immunology, vol. 2010, Article ID 683875, pp. 1-7 (2010).
Loos et al, "Development of an Fc-enhanced anti-B7-H3 monoclonal antibody with potent antitumor activity," Clinical Cancer Research, 18: 3834-3845 (2012).
Modak et al, "Monoclonal antibody 8H9 targets a novel cell surface antigen expressed by a wide spectrum of human solid tumors," Cancer Research, 61: 4048-4054 (2001).
Onda et al, "In vitro and in vivo cytotoxic activities of recombinant immunotoxin 8H9(Fv)-PE38 against breast cancer, osteosarcoma, and neuroblastoma," Cancer Research, 64: 1419-1424 (2004).
Vigdorovich et al, "Structure and T-cell inhibition properties of B7 family member, B7-H3," Structure, 21(5): 707-717 (2013).

(Continued)

*Primary Examiner* — Laura B Goddard
(74) *Attorney, Agent, or Firm* — Stephen C. Macevicz

(57) ABSTRACT

The invention is directed to novel antibody binding compounds specific for the human B7H3 and uses of such compounds for diagnostic and therapeutic purposes.

14 Claims, 5 Drawing Sheets

(56) References Cited

FOREIGN PATENT DOCUMENTS

| | | |
|---|---|---|
| WO | WO2016/106004 | 2/2016 |
| WO | WO/2016/106004 | 2/2016 |
| WO | WO/2016/033225 | 3/2016 |
| WO | WO2016/106004 | 6/2016 |

OTHER PUBLICATIONS

Xu et al, "MicroRNA miR-29 modulates expression of immunoinhibitory molecule B7-H3: potential implications for immune based therapy of human solid tumors," Cancer Research, 69(15): 6257-6281 (2009).

* cited by examiner

Off-rate ELISA
- 20ng bB7-H3 on NeutrAvidin coated well
- 18hr phage binding and 0-48hr wash
- qPCR

| Phage clone | 0hr | | 48hr | | Fold decrease |
|---|---|---|---|---|---|
| | bB7-H3 | WB | bB7-H3 | WB | |
| 1-1 | 1,632,996 | 2,963 | 788,876 | 504 | 2.1 |
| 1-2 | 1,129,414 | 4,071 | 686,881 | 568 | 1.6 |
| 1-4 | 1,839,265 | 1,869 | 734,634 | 165 | 2.5 |
| 1-5 | 1,496,510 | 1,734 | 508,562 | 487 | 2.9 |
| 1-7 | 2,123,056 | 2,371 | 1,024,938 | 232 | 2.1 |
| BD62 (WT) | 2,234,418 | 5,191 | 347,108 | 1,466 | 6.5 |
| 7.48 (neg. control) | 4,470 | 3,945 | 434 | 817 | --- |

Fig. 1C

Off-rate ELISA
- 20ng bB7-H3 on NeutrAvidin coated well
- 18hr phage binding and 0-48hr wash
- qPCR

| Phage clone | 0hr | | 48hr | | Fold decrease |
|---|---|---|---|---|---|
| | bB7-H3 | WB | bB7-H3 | WB | |
| 2-5 | 825,068 | 4,196 | 412,481 | 1,165 | 2.0 |
| 2-8 | 1,777,064 | 11,604 | 604,641 | 1,290 | 2.9 |
| Neg. control | 4,117 | 7,474 | 1,619 | 1,605 | --- |

Fig. 1F

ANTI-B7H3 BINDING COMPOUNDS AND USES THEREOF

This is an application filed under 35 USC 1.371(f) based on International Application serial number PCT/US2015/065645 filed 14 Dec. 2015, which claims priority from U.S. provisional applications Ser. No. 62/095,969 filed 14 Dec. 2014 and Ser. No. 62/105,135 filed 19 Jan. 2015. Each of the foregoing applications is incorporated herein by reference in its entirety.

BACKGROUND

B7H3 is a member of the B7 family of immune cell modulating molecules. It is expressed on the surface of a wide variety of tumor cells and tumor vasculature including neuroblastoma, melanoma, renal cell cancer, prostate cancer, colorectal cancer, pancreatic cancer, gastric cancer, breast cancer, ovarian cancer and small cell lung cancer[Cancer Res 61:4048-4054 (2001)]. Its expression on normal cells is inhibited by the microRNA, mi R-29, [Cancer Res 69(15): 6275-81 (2009)]. In humans the B7H3 protein is expressed in two forms, 21 g and 41 g. B7H3 expression has been correlated with poor prognosis in ovarian, RCC, NSCLC, pancreatic cancer, prostate cancer and colon cancer [Clin. Dev Immunol. 2010(683875): 1-7]. This finding and additional in vitro data have led to the hypothesis that B7H3 expression may inhibit cytotoxic lymphocyte activity [Structure 21(5):707-17 (2013)].

The mouse antibody, 8H9, binds to both the 21 g and 41 g forms of the protein. $1^{131}$ radio-conjugates of this antibody have been shown to be effective in reducing the size of neuroblastomas when administered intrathecally in limited human trials [J Neurooncol 97(3):409-18 (2010]. Fusion of a scFv from this antibody to the cytotoxic protein PE38 resulted in a molecule that was effective in eliminating B7H3-express xenografts in mice [Cancer Res 64:1419-24 (2004)]. Other anti-B7H3 antibodies have been developed with an Fc-enhanced component and has shown good reduction of human tumor xenografts in mouse oncology models [Clin Cancer Res 18-(4):3834-45 (2013)]. Given these results and the expression of B7H3 on a wide variety of solid tumors in humans, it would be highly desirable to engineer additional forms of this molecule which are more suitable for use as a human therapeutic. In particular, additional anti-B7H3 antibody binding compounds with decreased dissociation rates from its antibody-antigen complex would lead to better therapeutic compounds.

SUMMARY OF THE INVENTION

The present invention is directed to novel anti-B7H3 antibody binding compounds and methods of using the same. Aspects and embodiments of the present invention are exemplified in a number of implementations and applications, some of which are summarized below and throughout the specification.

In one aspect, the invention is directed to novel antibody binding compounds specific for the human B7H3 target molecule, wherein such antibody binding compounds comprise complementary determining regions defined by the following amino acid sequences:

TABLE 1

| CDR | Sequence | SEQ ID NO |
|-----|----------|-----------|
| HC1 | N-Y-D-I-N | 1 |
| HC2 | W-I-F-P-G-D-G-S-T-Q-Y-N-$X_1$-$X_2$-F-K-G | 2 |
| HC3 | Q-T-T-$X_3$-T-W-F-A-Y | 3 |
| LC1 | R-A-S-Q-$X_4$-I-S-$X_5$-$X_6$-L-H | 4 |
| LC2 | $X_7$-A-$X_8$-Q-$X_9$-$X_{10}$-$X_{11}$ | 5 |
| LC3 | Q-N-G-H-S-F-P-L-T | 6 | wherein:
$X_1$ is E, G or P;
$X_2$ is K or T;
$X_3$ is G, S, M or N;
$X_4$ is S or I,
$X_5$ is E, P, V, H, K or D;
$X_6$ is Y or W;
$X_7$ is H, Y, N or E;
$X_8$ is S or N;
$X_9$ is S or L:
$X_{10}$ is I, W or L;
$X_{11}$ is S or R;

The standard IUPAC single-letter codes for amino acids are used. In some embodiments, such antibody binding compounds have an affinity for the B7H3 target molecule that is characterized by an equilibrium binding constant of 100 nM or less, as measured by conventional techniques In some embodiments, where the framework residues $f_1$, $f_2$, $f_3$ and $f_4$ are those of SEQ ID NO: 7, or at least eighty percent identical thereto in the aggregate, compounds of the invention comprise the polypeptide of SEQ ID NO: 7 with one or more of the amino acid substitutions selected from the group consisting of: E62G, E62P, K63T, G102S, G102M and G102N. As used herein, reference to "percent identical in the aggregate" means a percent identical value is determined based on a comparison of all sequences simultaneously, as if they were a single contiguous sequence, in contrast to a comparison on a sequence-by-sequence basis. In other embodiments, where the framework residues $f_1$, $f_2$, $f_3$ and $f_4$ are those of SEQ ID NO: 7, or at least eighty percent identical thereto in the aggregate, compounds of the invention comprise the polypeptide of SEQ ID NO: 7 with at least two amino acid substitutions selected from the group consisting of: E62G, E62P, K63T, G102S, G102M and G102N. In some embodiments, where the framework residues $g_1$, $g_2$, $g_3$ and $g_4$ are those of SEQ ID NO: 8, or at least eighty percent identical thereto in the aggregate, compounds of the invention comprise the polypeptide of SEQ ID NO: 8 with one or more of the amino acid substitutions selected from the group consisting of: S28I, E31P, E31V, E31H, E31T, E31K, E31D, Y32W, H50Y, H50N, H50N, H50E, S52N, S54L, I55W, I55L, and S56R. In other embodiments, where the framework residues $g_1$, $g_2$, $g_3$ and $g_4$ are those of SEQ ID NO: 8, or at least eighty percent identical thereto in the aggregate, compounds of the invention comprise the polypeptide of SEQ ID NO: 8 with at least two amino acid substitutions selected from the group consisting of: S28I, E31P, E31V, E31H, E31T, E31K, E31D, Y32H, H50Y, H50N, H50E, S52N, S54L, I55W, I55L, and S56R. In some embodiments, the antibody binding compounds of the invention comprising a heavy chain and light chain as described in this paragraph which have an affinity for the human B7H3 target molecule that is characterized by an equilibrium binding constant of 100 nM or less, as measured by conventional techniques.

In another aspect, the invention is directed a new composition of matter comprising any one or more of the antibody binding compounds comprising a heavy chain and a light chain defined by the formulas (I) and (II):

$$\text{Heavy chain: } f_1\text{-HC1-}f_2\text{-HC2-}f_3\text{-HC3-}f_4 \quad (I)$$

$$\text{Light chain: } g_1\text{-LC1-}g_2\text{-LC2-}g_3\text{-LC3-}g_4 \quad (II)$$

wherein HC1, HC2, HC3, LC1, LC2 and LC3 are as described above in Table 1 (that is, SEQ ID NO: 1 through SEQ ID NO: 6), $f_1$, $f_2$, $f_3$ and $f_4$ are heavy chain framework residues, and $g_1$, $g_2$, $g_3$ and $g_4$ are light chain framework residues. In some embodiments, $f_1$, $f_2$, $f_3$ and $f_4$ are human heavy chain framework residues, and $g_1$, $g_2$, $g_3$ and $g_4$ are human light chain framework residues. In some embodiments f4 may include constant regions, CH1, CH2, CH3 and a hinge region. In some embodiments, antibody binding compounds comprise pairs of polypeptide chains of formula (I) and (II) assembled in an IgG format. In some embodiments, antibody binding compounds comprise pairs of polypeptide chains of formulas (I) and (II) assembled in a Fab format. In some of the foregoing embodiments, antibody binding compounds comprising heavy chains and light chains of formulas (I) and (II), respectively, are assembled by the formation of disulfide bonds therebetween. In some of the foregoing embodiments, each antibody binding compound of the invention has an affinity for the B7H3 target molecule that is characterized by an equilibrium binding constant of 100 nM or less, as measured by conventional techniques.

In another aspect, the invention is directed to novel antibody binding compounds specific for the human B7H3 target molecule, wherein such antibody binding compounds comprise complementary determining regions defined by the following amino acid sequences:

TABLE 2

| CDR | Sequence | SEQ ID NO |
|---|---|---|
| HC1 | N-Y-D-I-N | 1 |
| HC2 | W-I-F-P-G-D-G-S-T-Q-Y-N-G-K-F-K-G | 9 |
| HC3 | Q-T-T-G-T-W-F-A-Y | 10 |
| LC1 | R-A-S-Q-S-I-S-P-Y-L-H | 11 |
| LC2 | Y-A-S-Q-S-W-S | 12 |
| LC3 | Q-N-G-H-S-F-P-L-T | 6 |

In some embodiments of this aspect, antibody binding compounds have heavy and light chains defined by formulas (I) and (II), respectively, wherein $f_1$, $f_2$, $f_3$ and $f_4$ are heavy chain framework residues, and $g_1$, $g_2$, $g_3$ and $g_4$ are light chain framework residues. In further embodiments, $f_1$, $f_2$, $f_3$ and $f_4$ are human heavy chain framework residues, and $g_1$, $g_2$, $g_3$ and $g_4$ are human light chain framework residues. In some embodiments f4 may include constant regions, CH1, CH2, CH3 and a hinge region. In some embodiments, antibody binding compounds comprise pairs of polypeptide chains of formulas (I) and (II) assembled in an IgG format. In some embodiments, antibody binding compounds comprise pairs of polypeptide chains of formulas (I) and (II) assembled in a Fab format. In some of the foregoing embodiments, antibody binding compounds comprising heavy chains and light chains of formulas (I) and (II), respectively, are assembled by the formation of disulfide bonds therebetween. In some of the foregoing embodiments, each antibody binding compound of the invention has an affinity for the B7H3 target molecule that is characterized by an equilibrium binding constant of 100 nM or less, as measured by conventional techniques. In some embodiments, framework residues $f_1$, $f_2$, $f_3$ and $f_4$ are those of SEQ ID NO: 7, or at least eighty percent identical thereto in the aggregate, and framework residues $g_1$, $g_2$, $g_3$ and $g_4$ are those of SEQ ID NO: 8, or at least eighty percent identical thereto in the aggregate. In particular, embodiments of this aspect include an antibody binding compound comprising heavy chain polypeptide of SEQ ID NO: 13 and light chain polypeptide of SEQ ID NO: 14.

In another aspect, the invention is directed to novel antibody binding compounds specific for the human B7H3 target molecule, wherein such antibody binding compounds comprise complementary determining regions defined by the following amino acid sequences:

TABLE 3

| CDR | Sequence | SEQ ID NO |
|---|---|---|
| HC1 | N-Y-D-I-N | 1 |
| HC2 | W-I-F-P-G-D-G-S-T-Q-Y-N-E-T--F-K-G | 15 |
| HC3 | Q-T-T-G-T-W-F-A-Y | 10 |
| LC1 | R-A-S-Q-S-I-S-K-Y-L-H | 16 |
| LC2 | Y-A-N-Q-S-I-R | 17 |
| LC3 | Q-N-G-H-S-F-P-L-T | 6 |

In some embodiments of this aspect, antibody binding compounds have heavy and light chains defined by formulas (I) and (II), respectively, wherein $f_1$, $f_2$, $f_3$ and $f_4$ are heavy chain framework residues, and $g_1$, $g_2$, $g_3$ and $g_4$ are light chain framework residues. In further embodiments $f_1$, $f_2$, $f_3$ and $f_4$ are human heavy chain framework residues, and $g_1$, $g_2$, $g_3$ and $g_4$ are human light chain framework residues. In some embodiments f4 may include constant regions, CH1, CH2, CH3 and a hinge region. In some embodiments, antibody binding compounds comprise pairs of polypeptide chains of formulas (I) and (II) assembled in an IgG format. In some embodiments, antibody binding compounds comprise pairs of polypeptide chains of formulas (I) and (II) assembled in an Fab format. In some of the foregoing embodiments, antibody binding compounds comprising heavy chains and light chains of formulas (I) and (II), respectively, are assembled by the formation of disulfide bonds therebetween. In some of the foregoing embodiments, each antibody binding compound of the invention has an affinity for the B7H3 target molecule that is characterized by an equilibrium binding constant of 100 nM or less, as measured by conventional techniques. In some embodiments, framework residues $f_1$, $f_2$, $f_3$ and $f_4$ are those of SEQ ID NO: 7, or at least eighty percent identical thereto in the aggregate, and framework residues $g_1$, $g_2$, and $g_3$ and $g_4$ those of SEQ ID NO: 8, or at least eighty percent identical thereto in the aggregate. In particular, embodiments of this aspect include an antibody binding compound comprising heavy chain polypeptide of SEQ ID NO: 18 and light chain polypeptide of SEQ ID NO: 19.

In another aspect, the invention is directed to novel antibody binding compounds specific for the human B7H3 target molecule, wherein such antibody binding compounds comprise complementary determining regions defined by the following amino acid sequences:

TABLE 4

| CDR | Sequence | SEQ ID NO |
|---|---|---|
| HC1 | N-Y-D-I-N | 1 |
| HC2 | W-I-F-P-G-D-G-S-T-Q-Y-N-P-K-F-K-G | 20 |
| HC3 | Q-T-T-G-T-W-F-A-Y | 10 |
| LC1 | R-A-S-Q-S-I-S-T-Y-L-H | 21 |

TABLE 4-continued

| CDR | Sequence | SEQ ID NO |
|---|---|---|
| LC2 | E-A-S-Q-S-I-S | 22 |
| LC3 | Q-N-G-H-S-F-P-L-T | 6 |

In some embodiments of this aspect, antibody binding compounds have heavy and light chains defined by formulas (I) and (II), respectively, wherein $f_1$, $f_2$, $f_3$ and $f_4$ are heavy chain framework residues, and $g_1$, $g_2$, $g_3$ and $g_4$ are light chain framework residues. In further embodiments, $f_1$, $f_2$, $f_3$ and $f_4$ are human heavy chain framework residues, and $g_1$, $g_2$, $g_3$ and $g_4$ are human light chain framework residues. In some embodiments f4 may include constant regions, CH1, CH2, CH3 and a hinge region. In some embodiments, antibody binding compounds comprise pairs of polypeptide chains of formulas (I) and (II) assembled in an IgG format. In some embodiments, antibody binding compounds comprise pairs of polypeptide chains of formulas (I) and (II) assembled in an Fab format. In some of the foregoing embodiments, antibody binding compounds comprising heavy chains and light chains of formulas (I) and (II), respectively, are assembled by the formation of disulfide bonds therebetween. In some of the foregoing embodiments, each antibody binding compound of the invention has an affinity for the B7H3 target molecule that is characterized by an equilibrium binding constant of 100 nM or less, as measured by conventional techniques. In some embodiments, framework residues $f_1$, $f_2$, $f_3$ and $f_4$ are those of SEQ ID NO: 7, or at least eighty percent identical thereto in the aggregate, and framework residues $g_1$, $g_2$, $g_3$ and $g_4$ are those of SEQ ID NO: 8, or at least eighty percent identical thereto in the aggregate. In particular, embodiments of this aspect include an antibody binding compound comprising heavy chain polypeptide of SEQ ID NO: 23 and light chain polypeptide of SEQ ID NO: 24.

In another aspect, the invention is directed to novel antibody binding compounds specific for the human B7H3 target molecule, wherein such antibody binding compounds comprise complementary determining regions defined by the following amino acid sequences:

TABLE 5

| CDR | Sequence | SEQ ID NO |
|---|---|---|
| HC1 | N-Y-D-I-N | 1 |
| HC2 | W-I-F-P-G-D-G-S-T-Q-Y-N-E-K-F-K-G | 25 |
| HC3 | Q-T-T-G-T-W-F-A-Y | 10 |
| LC1 | R-A-S-Q-S-I-S-H-Y-L-H | 26 |
| LC2 | Y-A-S-Q-S-L-S | 27 |
| LC3 | Q-N-G-H-S-F-P-L-T | 6 |

In some embodiments of this aspect, antibody binding compounds have heavy and light chains defined by formulas (I) and (II), respectively, wherein $f_1$, $f_2$, $f_3$ and $f_4$ are heavy chain framework residues, and $g_1$, $g_2$, $g_3$ and $g_4$ are light chain framework residues. In further embodiments, $f_1$, $f_2$, $f_3$ and $f_4$ are human heavy chain framework residues, and $g_1$, $g_2$, $g_3$ and $g_4$ are human light chain framework residues. In some embodiments f4 may include constant regions, CH1, CH2, CH3 and a hinge region. In some embodiments antibody binding compounds comprise pairs of polypeptide chains of formulas (I) and (II) assembled in an IgG format. In some embodiments, antibody binding compounds comprise pairs of polypeptide chains of formulas (I) and (II) assembled in an Fab format. In some of the foregoing embodiments, antibody binding compounds comprising heavy chains and light chains of formulas (I) and (II), respectively, are assembled by the formation of disulfide bonds therebetween. In some of the foregoing embodiments, each antibody binding compound of the invention has an affinity tm the B7H3 target molecule that is characterized by an equilibrium binding constant of 100 nM or less, as measured by conventional techniques. In some embodiments, framework residues $f_1$, $f_2$, $f_3$ and $f_4$ are those of SEQ ID NO: 7, or at least eighty percent identical thereto in the aggregate, and framework residues $g_1$, $g_2$, $g_3$ and $g_4$ are those of SEQ ID NO: 8, or at least eighty percent identical thereto in the aggregate. In particular, embodiments of this aspect include an antibody binding compound comprising heavy chain polypeptide of SEQ ID NO: 28 and light chain polypeptide of SEQ ID NO: 29.

In another aspect, the invention is directed to novel antibody binding compounds specific for the human B7H3 target molecule, wherein such antibody binding compounds comprise complementary determining regions defined by the following amino acid sequences:

TABLE 6

| CDR | Sequence | SEQ ID NO |
|---|---|---|
| HC1 | N-Y-D-I-N | 1 |
| HC2 | W-I-F-P-G-D-G-S-T-Q-Y-N-E-K-F-K-G | 25 |
| HC3 | Q-T-T-G-T-W-F-A-Y | 10 |
| LC1 | R-A-S-Q-S-I-S-P-Y-L-H | 11 |
| LC2 | H-A-S-Q-S-I-S | 30 |
| LC3 | Q-N-G-H-S-F-P-L-T | 6 |

In some embodiments of this aspect, antibody binding compounds have heavy and light chains defined by formulas (I) and (II), respectively, wherein $f_1$, $f_2$, $f_3$ and $f_4$ and are heavy chain framework residues, and $g_1$, $g_2$, $g_3$ and $g_4$ are light chain framework residues. In further embodiments, $f_1$, $f_2$, $f_3$ and $f_4$ are human heavy chain framework residues, and $g_1$, $g_2$, $g_3$ and $g_4$ are human light chain framework residues. In some embodiments f4 may include constant regions, CH1, CH2, CH3 and a hinge region. In some embodiments, antibody binding compounds comprise pairs of polypeptide chains of formulas (I) and (II) assembled in an IgG format. In some embodiments, antibody binding compounds comprise pairs of polypeptide chains of formulas (I) and (II) assembled in an Fab format. In some of the foregoing embodiment, antibody binding compounds composing heavy chains and light chains of formulas (I) and (II), respectively, are assembled by the formation of disulfide bonds therebetween. In some of the foregoing embodiment, each antibody binding compound of the invention has an affinity for the B7H3 target molecule that is characterized by an equilibrium binding constant of 100 nM or less, as measured by conventional techniques. In some embodiments, framework residues $f_1$, $f_2$, $f_3$ and $f_4$ are those of SEQ ID NO: 7, or at least eighty percent identical thereto in the aggregate, and framework residues $g_1$, $g_2$, $g_3$ and $g_4$ are those of SEQ ID NO: 8, or at least eighty percent identical thereto in the aggregate. In particular, embodiments of this aspect include an antibody binding compound comprising heavy chain polypeptide of SEQ ID NO: 31 and light chain polypeptide of SEQ ID NO: 32.

In another aspect, the invention is directed to novel antibody binding compounds specific for the human B7H3 target molecule, wherein such antibody binding compounds comprise complementary determining regions defined by the following amino acid sequences:

TABLE 7

| CDR | Sequence | SEQ ID NO |
| --- | --- | --- |
| HC1 | N-Y-D-I-N | 1 |
| HC2 | W-I-F-P-G-D-G-S-T-Q-Y-N-E-K-F-K-G | 25 |
| HC3 | Q-T-T-S-T-W-F-A-Y | 33 |
| LC1 | R-A-S-Q-I-I-S-D-Y-L-H | 34 |
| LC2 | Y-A-S-Q-L-I-S | 35 |
| LC3 | Q-N-G-H-S-F-P-L-T | 6 |

In some embodiments of this aspect, antibody binding compounds have heavy and light chains defined by formulas (I) and (II), respectively, wherein $f_1$, $f_2$, $f_3$ and $f_4$ are heavy chain framework residues, and $g_1$, $g_2$, $g_3$ and $g_4$ are light chain framework residues. In further embodiments, $f_1$, $f_2$, $f_3$ and $f_4$ are human heavy chain framework residues, and $g_1$, $g_2$, $g_3$ and $g_4$ are human light chain framework residues. In some embodiments f4 may include constant regions, CH1, CH2, CH3 and a hinge region. In some embodiments, antibody binding compounds comprise pairs of polypeptide chains of formulas (I) and (II) assembled in an IgG format. In some embodiments, antibody binding compounds comprise pairs of polypeptide chains of formulas (I) and (II) assembled in an Fab format. In some of the foregoing embodiments, antibody binding compounds comprising heavy chains and light chains of formulas (I) and (II), respectively, are assembled by the formation of disulfide bonds therebetween. In some of the foregoing embodiments, each antibody binding compound of the invention has an affinity for the B7H3 target molecule that is characterized by an equilibrium binding constant of 100 nM of less, as measured by conventional techniques. In some embodiments, framework residues $f_1$, $f_2$, $f_3$ and $f_4$ are those of SEQ ID NO: 7, or at least eighty percent identical thereto in the aggregate, and framework residues $g_1$, $g_2$, $g_3$ and $g_4$ are those of SEQ ID NO: 8, or at least eighty percent identical thereto in the aggregate. In particular, embodiments of this aspect include an antibody binding compound comprising heavy chain polypeptide of SEQ ID NO: 36 and light chain polypeptide of SEQ ID NO: 37.

In another aspect, the invention is directed to novel antibody binding compounds specific for the human B7H3 target molecule, wherein such antibody binding compounds comprise complementary determining regions defined by the following amino acid sequences:

TABLE 8

| CDR | Sequnce | SEQ ID NO |
| --- | --- | --- |
| HC1 | N-Y-D-I-N | 1 |
| HC2 | W-I-F-P-G-D-G-S-T-Q-Y-N-E-K-F-K-G | 25 |
| HC3 | Q-T-T-G-T-W-F-A-Y | 10 |
| LC1 | R-A-S-Q-S-I-S-E-Y-L-H | 38 |
| LC2 | H-A-S-Q-S-I-S | 30 |
| LC3 | Q-N-G-H-S-F-P-L-T | 6 |

In some embodiments of this aspect, antibody binding compounds have heavy and light chains defined by formulas (I) and (II), respectively, wherein $f_1$, $f_2$, $f_3$ and $f_4$ are heavy chain framework residues, and $g_1$, $g_2$, $g_3$ and $g_4$ are light chain framework residues. In further embodiments, $f_1$, $f_2$, $f_3$ and $f_4$ are human heavy chain framework residues, and $g_1$, $g_2$, $g_3$ and $g_4$ are human light chain framework residues. In some embodiments f4 may include constant regions, CH1, CH2, CH3 and a hinge region. In some embodiments, antibody binding compounds comprise pairs of polypeptide chains of formulas (I) and (II) assembled in an IgG format. In some embodiments, antibody binding compounds comprise pairs of polypeptide chains of formulas (I) and (II) assembled in an Fab format. In some of the foregoing embodiments, antibody binding compounds comprising heavy chains and light chains of formulas (I) and (II), respectively, are assembled by the formation of disulfide bonds therebetween. In some of the foregoing embodiments, each antibody binding compound of the invention has an affinity for the B7H3 target molecule that is characterized by an equilibrium binding constant of 100 nM or less, as measured by conventional techniques. In some embodiments, framework residues $f_1$, $f_2$, $f_3$ and $f_4$ are those of SEQ ID NO: 7, or at least eighty percent identical thereto in the aggregate, and framework residues $g_1$, $g_2$, $g_3$ and $g_4$ are those of SEQ ID NO: 8, or at least eighty percent identical thereto in the aggregate. In particular, embodiments of this aspect include an antibody binding compound comprising heavy chain polypeptide of SEQ ID NO: 7 and light chain polypeptide of SEQ ID NO: 8.

In some embodiments, the above antibody binding compounds of the invention are each selected with an affinity for the B7H3 target molecule that is characterized by an equilibrium binding contain of 100 nM or less; as measured by conventional techniques; or 10 nM or less, as measured by conventional techniques; or 1 nM or less, as measured by conventional techniques.

In some embodiments, the invention also includes pharmaceutical compositions comprising at least one of the foregoing antibody binding compounds. The invention further provides the use of an antibody binding compound of the invention in the preparation of a medicament for the therapeutic and/or prophylactic treatment of a disorder, such as a cancer, a tumor, and/or a cell proliferative disorder. In some embodiments, pharmaceutical compositions of the invention comprise one or more antibody binding compounds of the invention and a carrier. In some embodiments, the carrier is pharmaceutically acceptable.

In another aspect, the invention provides nucleic acids encoding antibody binding compounds of the invention.

In yet another aspect, the invention provides vectors comprising a nucleic acid of the invention.

In one aspect, the invention provides host cells comprising a nucleic acid or a vector of the invention. A vector can be of any type, for example, a recombinant vector such as an expression vector. Any of a variety of host cells can be used. In one embodiment, a host cell is a prokaryotic cell, for example, E. coli. In another embodiment, a host cell is a eukaryotic cell, for example a mammalian cell such as Chinese Hamster Ovary (CHO) cell.

In a further aspect, the invention provides methods of making an antibody binding compound of the invention. For example, the invention provides methods of making an antibody binding compound of the invention (which, as defined herein includes without limitation full length antibody and fragments thereof), said method comprising expressing in a suitable host cell a recombinant vector of the invention encoding the antibody (or fragment thereof), and recovering the antibody or fragment.

In one aspect, the invention provides an article of manufacture comprising a container; and a composition contained within the container, wherein the composition comprises one or more antibody binding compounds of the invention. In one embodiment, the composition comprises a nucleic acid of the invention. In another embodiment, a composition comprising an antibody binding compound further comprises a carrier, which in some embodiments is pharmaceutically acceptable. In one embodiment, an article of manufacture of the invention further comprises instructions for administering the composition (e.g., an antibody) to an individual (such as instructions for any of the methods described herein).

In another aspect, the invention provides a kit comprising a first container computing a composition comprising one or more antibody binding compounds of the invention; and a second container comprising a buffer. In one embodiment, the buffer is pharmaceutically acceptable. In one embodiment, a composition comprising an antibody further comprises a carrier, which in some embodiments is pharmaceutically acceptable. In another embodiment, a kit further comprises instructions for administering the composition (e.g., the antibody) to an individual.

In a further aspect, the invention provides use of an antibody binding compound of the invention in the preparation of a medicament for the therapeutic and/or prophylactic treatment of a disorder, such as a cancer, a tumor, and/or a cell proliferative disorder.

These above-characterized aspects and embodiments, as well as other aspects and embodiments, of the present invention are exemplified in a number of illustrated implementations and applications, some of which are shown in the figures and characterized in the claims section that follows. However, the above summary is not intended to describe each illustrated embodiment or every implementation of the present invention.

BRIEF DESCRIPTIONS OF THE DRAWINGS

FIG. 1C is a table giving dissociation or off-rate data of an antibody binding compound of the invention.

FIG. 1F is a table showing ELISA off-rate data for invention compounds 2-5 and 2-8.

DETAILED DESCRIPTION OF THE INVENTION

Figures 1A, 1B:
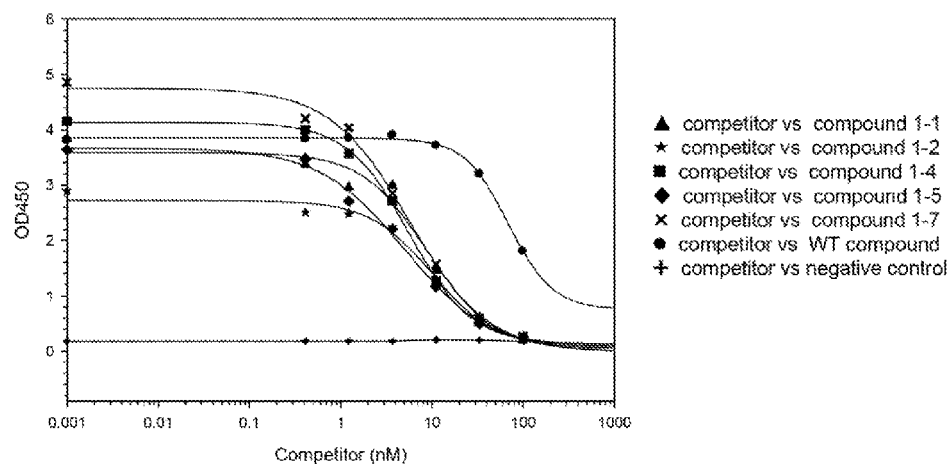
FIG. 1A illustrates competitive binding data for an antibody binding compound of the invention.
FIG. 1B is a table giving parameter values related to competitive binding of a antibody binding compound of the invention.
Figures 1D, 1E:
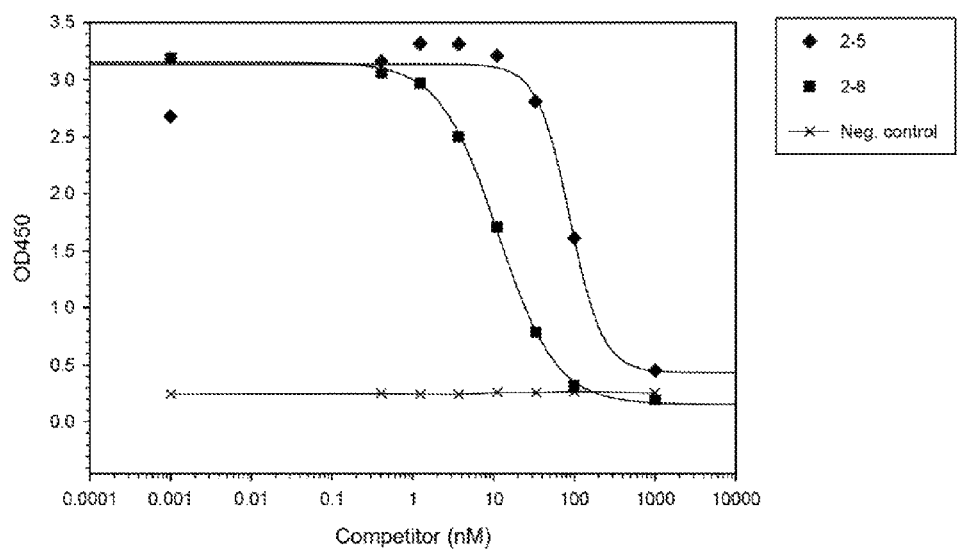
FIG. 1D shows competition ELISA data for invention compounds 2-5 and 2-8.
FIG. 1E is a table showing competition ELISA data for invention compounds 2-5 and 2-8.

The practice of the present invention may employ, unless otherwise indicated, conventional techniques of organic chemistry, molecular biology, cell biology, biochemistry, and therapeutic antibody development, which are within the skill of the art. Specific illustrations of suitable techniques can be had by reference to the examples below, with the understanding that other equivalent techniques and procedures can be used. Conventional techniques and guidance related to making and using the invention may be found in standard treatises and laboratory manuals, such as *Genome Analysis: A Laboratory Manual Series* (Vols. I-IV); *PCR Primer: A Laboratory Manual; Phage Display: A Laboratory Manual*; and *Molecular Cloning: A Laboratory Manual* (all from Cold Spring Harbor Laboratory Press); Sidhu, editor, Phage Display in Biotechnology and Drug Discovery (CRC Press, 2005); Lutz and Bornscheuer, Editors, Protein Engineering Handbook (Wiley-VCH, 2009); Hermanson, Bioconjugate Techniques, Second Edition (Academic Press, 2008); Dubel (Editor), Handbook of Therapeutic Antibodies (Wiley-VCH, 2007); Al-Rubeai (Editor), Antibody Expression and Production (Springer, 2011); An (Editor), Therapeutic Monoclonal Antibodies: From Bench to Clinic (Wiley, 2009); and the like. Further teaching and guidance for developing and using antibody binding compounds are found in the following U.S. Pats. which are incorporated herein by reference U.S. Pat. Nos. 6,627,196; 8,710,189; 8,846,871; 7,524,502; and the like.

Antibody Binding Compound Formats

An antibody binding compound of the invention may be produced and or used in a variety of formats, including but not limited to, a monoclonal antibody, a monoclonal antibody of a selected isotype, an antibody fragment, a humanized monoclonal antibody, a glycosylated monoclonal antibody, an antibody conjugated to another moiety that imparts an added functionality, e.g. cytotoxicity, to the resulting conjugate, and the like. Selection of a particular format may depend on a variety of factors, including but not limited to, tissue accessibility, whether ADCC is desired, solubility, whether bi-specificity is desired, ease of manufacture, and the like.

The present invention encompasses antibody fragments. In certain circumstances there are advantages of using antibody fragments, rather than whole antibodies. The smaller size of the fragments allows for rapid clearance, and may lead to improved access to solid tumors. Various techniques are available for the production of antibody fragments. Antibody fragments may be derived via proteolytic digestion of intact antibodies (see, e.g., Morimoto et al., Journal of Biochemical and Biophysical Methods 24:107-117 (1992); and Brennan et al., Science, 229:81 (1985)). Antibody fragments may also be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life composing a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv) (see, e.g., WO 93/16185; U.S. Pat. Nos. 5,571,894 and 5,587,458). Fv and sFv are the only species with intact combining sites that are devoid of constant regions; thus, they are suitable for reduced non-specific binding during in vivo use. sFv fusion proteins may be constructed to yield fusion of an effector protein at either the amino or the carboxy terminus of an sFv. See Antibody Engineering. ed. Borrebaeck, supra. The antibody fragment may also be a "linear antibody," e.g., as described, for example, in U.S. Pat. No. 5,641,870. Such linear antibody fragments may be monospecific or bispecific.

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:3237-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

Humanized antibodies of the invention include those that have amino acid substitutions in the framework region (FR) and affinity maturation variants with changes in the grafted CDRs. In some embodiments, the antibodies of the invention further comprise changes in amino acid residues in the Fc region that lead to improved effector function including enhanced complement dependent cytotoxicity (CDC) and/or antibody dependent cellular cytotoxicity (ADCC) function and B-cell killing. Other antibodies of the invention include those having specific changes that improve stability. In some embodiments, the antibodies of the invention are of the IgG class (e.g., IgG1 or IgG4).

The invention includes bispecific antibodies wherein one of the specificities is determined by a compound of the invention. Bispecific antibodies are monoclonal, preferably human or humanized, antibodies that have binding specificities for at least two different antigens. In the present case, one of the binding specificities is for antigen of the inventive compounds and the other is for any other antigen. Bispecific antibodies may also be used to localize cytotoxic agents to cells which express the antigen of the inventive compounds. These antibodies possess an arm binding to the inventive compound antigen and an arm which binds the cytotoxic agent (e.g., saporin, anti-interferon-α, vinca alkaloid, ricin A chain, methotrexate or radioactive isotope hapten). Bispecific antibodies may also be used to localize cytotoxic cells to cells which express the antigen of the inventive compound (anti-CD3, anti-CD16, etc). Bispecific antibodies can be prepared as full length antibodies or antibody fragments (e.g., F(ab')2 bispecific antibodies, scFv fusions or the like). Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Similar procedures are disclosed in WO 93/08829 published May 13, 1993, and in Traunecker et al., EMBO J., 10: 3655 (1991).

In some embodiments, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

Antibody binding compounds of the invention may be glycosylated. Addition of glycosylation sites to an antibody binding compound is conveniently accomplished by altering the amino acid sequence such that it contains one or more of the tripeptide sequences for N-linked glycosylation sites, or so that it contains one or more serine or threonine residues to the sequence of the original antibody tor O-linked glycosylation sites.

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies, with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

Such variants any have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336:1239-1249 (2004): Yamane-Ohnuki et al. Biotech Bioeng. 87:614 (2004). Examples of cell lines producing defucosylated antibodies include Lee13 CHO cells deficient in protein fucosylation (Ripka et al. Arch. Biochem. Biophys. 249:533-545 (1986); US Pat Appl No US 2003/0157108 Al. Presta, L; and WO 2004/056312 Al. Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004))

In some embodiments, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Antibody binding compounds of the present invention can be further modified to contain additional nonproteinaceous moieties that are known in the art and readily available. Preferably, the moieties suitable for derivatization of the antibody binding compounds are water soluble polymers. Non-limiting examples of water soluble polymers include, but are not limited to, polyethylene glycol (PEG), copolymers of ethylene glycol-propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Antibody binding compounds of the invention may include chimeric antigen receptor compounds (CARs), whenever a particular antigen serves as a target for cytotoxic T cells, such as a tumor antigen. CARs permit MHC-independent targeting of cytotoxic T cells and are made by fusing antigen-binding components of the invention with transmembrane and signaling components capable of eliciting a cytotoxic T cell response whenever the antigen-specific component binding to its target. Exemplary references teaching the manufacture and application of CARs include the following references that are incorporated herein by reference: U.S. Pat. No. 8,822,647; and U.S. patent publications 2014/0134142; 2014/0314795; 2012/0148552; 2013/0288368; and the like.

Expression Systems

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures. Many vectors are available. The choice of vector depends in part on the host cell to be used. Generally, preferred host cells are of either prokaryotic to eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Polynucleotide-sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or can be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct at and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactanase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al., (1980) Cell 20:269) using linkers or adaptors to supply any required restriction sites.

In one aspect of the invention, each citron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA, and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli*λ 1776 (ATCC 31,537) and *E. coli* RV308 (ATCC 31,608) are also suitable. These examples are illustrative rather than limning. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well-known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initialed after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD, and/or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al., (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun, (2000) J. Biol. Chem. 275: 17106-17113; Arie et al., (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some *E. coli* protease-deficient strains are available and described in, for example, Joly et al., (1998), supra; Georgiou et al., U.S. Pat. No. 5,264,365; Georgiou et al., U.S. Pat. No. 5,508,192; Hara el al., Microbial Drug Resistance, 2:63-72 (1996).

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41 kD cell wall protein from *Staphylococcus aureus* which binds with a high affinity to the Fe region of antibodies. Lindmark et al., (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

Generating antibody binding compounds using eukaryotic host cells. Vector components for eukaryotic expression generally include, but are not limited to, one or more of the following: a signal sequence, an origin of replication, one or more marker genes, an enhancer element, a promoter, and a transcription termination sequence.

Signal Sequence Component. A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA encoding a signal sequence is ligated in reading frame to DNA encoding the antibody.

Origin of Replication. Generally, an origin of replication component is not needed for mammalian expression vectors. For example, the SV40 origin may typically be used only because it contains the early promoter.

Selection Gene Component. Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin. Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc. For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096). Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycoside antibiotic, e.g., kanamycin, neomycin, or G418. See U.S. Pat. No. 4,965,199.

Promoter Component. Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Antibody polypeptide transcription from vectors in mammalian host cells is controlled, for example, by promoters obtained from the genomes of viruses such as polyoma virus, fowlpox virus, adenovirus (such as Adenovirus 2). bovine papilloma virus, avian sarcoma virus, cytomegalovirus, a retrovirus, hepatitis-B virus, and Simian Virus 40 (SV40), from heterologous mammalian promoters, e.g., the actin promoter or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

Enhancer Element Component. Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

Transcription Termination Component. Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

Selection and Transformation of Host Cells. Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)), mouse sertoli cells (TM4, Mather. Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065): mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2). Host cells are transformed with the above-described expression or cloning vectors for antibody production and cultured in conventional nutrient media modified as appropriate for inducing promoters, selecting transformants, or amplifying the genes encoding the desired sequences.

Culturing the Host Cells. The host cells used to produce an antibody of this invention may be cultured in a variety of media. Commercially available media such as Ham's F10 (Sigma). Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. Meth. Enz. 58:44 (1979), Barnes et al., Anal. Biochem. 102:255 (1980). U.S. Pat. Nos. 4,767,704; 4,657,866; 4,927, 762; 4,560,655; or U.S. Pat. No. 5,122,469; WO 90/03430; WO 87/00195; or U.S. Patent Re. 30,985 may be used as culture media for the host cells. Any of these media may be supplemented as necessary with hormones and or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions such as temperature, pH, and the like, are those previously used with the host cell selected for expression, and will be apparent to the ordinarily skilled artisan.

Purification of product. When using recombinant techniques, the antibody can be produced intracellularly, or directly secreted into the medium. If the antibody is produced intracellularly, as it first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, β2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N. J.) is useful for purification. Other techniques for protein purification such as fractionation on an ion-exchange column, ethanol precipitation. Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Affinity Determination

As mentioned above, some embodiments of the compounds of the invention have an affinity for human B7H3 within identified ranges as measured in conventional assays detailed below Human B7H3 for use in such assays may be obtained from commercial sources, e.g. R&D Systems (Minneapolis, Minn.).

"Affinity" or "binding affinity" means the strength of the sum total of noncovalent interactions between a single binding site of a molecule (e.g. an antibody binding compound) and its binding partner (e.g., an antigen). Unless indicated otherwise, as used herein, "binding affinity" refers to intrinsic binding affinity which reflects all interaction between members of a binding pair (e.g., antibody binding compound and antigen). The affinity of a molecule X for its partner Y can generally be represented by the dissociation constant (Kd). Desirably the Kd is $1 \times 10^{-7}$, $1 \times 10^{-8}$, $5 \times 10^{-8}$, $1 \times 10^{-9}$, $3 \times 10^{-9}$, $5 \times 10^{-9}$ or even $1 \times 10^{-10}$ or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In some embodiments, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol. Biol. 293:865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620). 100 pM or 26 [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 μg/ml (0.2 μM) before injection at a flow rate of 5 μl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate at approximately 25 μl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol. 293:865-881. If the on-rate exceeds $10^8 M^{-1} S^{-2}$ by the surface plasmon resonance assay above, then the on-rate can be determined by using a fluorescent quenching technique that measures the increase or decrease in fluorescence emission intensity (excitation=295 nm; emission=340 nm, 16 mm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-

3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 uM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissipation constant (Kd) was calculated as the ratio $k_{off}/k_{on}$. See, e.g., Chen, Y., et al., (1999) J. Mol. Biol. 293:865-881. However, if the on-rate exceeds $10^6 M^{-1} S^{-1}$ by the surface plasmon resonance assay above, then the on-rate is preferably determined by using a fluorescent quenching technique that measures the increase or decrease in fluorescence emission intensity (excitation=295 nm: emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

The efficiency of selecting particular embodiments with desired binding properties depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al.,Proteins, 8: 309-314 (1990) and in WO 92/09690, and a low coating density of antigen as described in Marks et al., Biotechnol., 10: 779-783 (1992). The high affinity-binding phages can then be captured by streptavidin-coated paramagnetic beads. Such "equilibrium capture" allows the antibodies to be selected according to their affinities of binding, with sensitivity dial permits isolation of mutant clones with as little as two-fold higher affinity from a great excess of phages with lower affinity. Conditions used in washing phages bound to a solid phase can also be manipulated to discriminate on the basis of dissociation kinetics.

Therapeutic Conjugates

The invention also provides immunoconjugates (interchangeably termed "antibody-drug conjugates" or "ADC"), comprising any of the antibody or antibody fragments described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e., drugs to kill or inhibit tumor cells in the treatment of cancer (Syrigos and Epenetos (1999) Anticancer Research 19:605-614; Niculeseu-Duvaz and Springer (1997) Adv. Drg.-Del. Rev. 26: 151-172; U.S. Pat. No. 4,975,278) allows targeted-delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents in Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al., (2000) Bioorganic & Med. Chem. Letters 10: 1025-1028; Mandler et al., (2002) Bioconjugate Chem. 13:786-791), maytansinoids (EP 1391213; Liu et al., (1996) Proc. Natl. Acad. Sci. USA 93:8618-8623), auristatins and calicheamicin (Lode et al., (1998) Cancer Res. 58:2928; Hinman et al., (1993) Cancer Res. 53:3336-3342). The toxins may exert their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al., (2000) Eur. Jour. Nucl. Med. 27(7):766-77; Wiseman et al., (2002) Blood 99(12):4336-42; Witzig et al., (2002) J. Clin. Oncol. 20(10): 2453-63; Witzig et al., (2002) J. Clin. Oncol. 20(15):3262-69) Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198, 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is approved for the treatment of cancers dial express CanAg, such as colon, pancreatic, gastric, and others. MLN-2704 (Millennium Pharm., BZL Biologies, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al., (2003) Nature Biotechnology 21(7):778-784) and are under therapeutic development.

Chemotherapeutic agents useful in the generation of immunoconjugates are described herein, (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins. *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include 212Bi, 131I, 131In, 90Y, and 186Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl substrate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

Preparation of Antibody Minding Compound-Drug Conjugates. In the antibody binding compound-drug conjugates (ADC) of the invention, an antibody (Ab) is conjugated to one or more drug moieties (D), e.g. about 1 to about 20 drug moieties per antibody binding compound, through a linker (L). The ADC of Formula 1 may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

The linker may be composed of one or more linker components. Exemplary linker components include 6-maleimidocaproyl ("MC"), maleimidopropanoyl ("MP"), valine-citrulline ("val-cit"), a alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-I carboxylate ("SMCC"), and N-Succinimidyl (4-iodo-acetyl)aminobenzoate ("SIAB"). Additional linker components are known in the art and some are described herein. See also "Monomethylvaline Compounds Capable of Conjugation to Ligands," U.S. Ser. No. 10/983,340, filed Nov. 5, 2004, the contents of which are hereby incorporated by reference in its entirely.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, at a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may lead with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium metaperiodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146: U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBi esters, haloformates, and acid halides; (ii) alkyl and benzyl halides such as haloacetamides; (iii) aldehydes, ketones, carboxyl, and maleimide groups.

Alternatively, a fusion protein composing the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

In another embodiment, the antibody binding regions may be fused with T cell transmembrane and signaling components to form a chimeric antigen receptor (CAR), as described more fully above.

Therapeutic Formulations

Therapeutic formulations comprising an antibody binding compound of the invention are prepared for storage by mixing the antibody having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagme, histidine, arginine, or lysine; monosaccharides, disaccharides, and other carbohydrates including glucose, mannose, or dextrins; chelating agents such as EDIA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved for example, it the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Therapeutic Treatments

In some embodiments, antibody binding compounds of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Method of treatment using compounds of the present invention involves the administration of an antibody binding compound of the invention to an animal or human patient, followed at intervals by subsequent doses of equal or smaller doses such that a target serum concentration is achieved and maintained during treatment. In some embodiments, maintenance doses are delivered by bolus delivery, preferably by subcutaneous bolus administration, making treatment convenient and cost-effective for the patient and health care professionals.

Where combined administration of a chemotherapeutic agent (other than an antracycline) is desired, the combined administration includes co-administration, using separate formulations or a single pharmaceutical formulation, and consecutive administration in either order, wherein preferably there is a time period while both (or all) active agents simultaneously exert their biological activities. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed.. M. C. Perry, Williams & Wilkins, Baltimore, Md. (1992). The chemotherapeutic agent may precede, or follow administration of the antibody binding compound or may be given simultaneously therewith.

Depending on the type and severity of the disease, about 1 µg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy is easily monitored by conventional techniques and assays.

According to the invention, dosage regimens may include an initial dose of antibody binding compound of 6 mg/kg, 8 mg/kg, or 12 mg/kg delivered by intravenous or subcutaneous infusion, followed by subsequent weekly maintenance doses of 2 mg/kg by intravenous infusion, intravenous bolus injection, subcutaneous infusion, or subcutaneous bolus injection. Where the antibody is well-tolerated by the patient, the time of infusion may be reduced.

Alternatively, the invention includes an initial dose of 12 mg/kg antibody binding compound, followed by subsequent maintenance doses of 6 mg/kg once per 3 weeks.

Another dosage regimen involves an initial dose of 8 mg/kg antibody binding compound, followed by 6 mg/kg once per 3 weeks.

Still another dosage regimen involve an initial dose of 8 mg/kg antibody binding compound, followed by subsequent maintenance doses of 8 mg/kg once per week or 8 mg/kg once every 2 to 3 weeks.

As an alternative regimen, initial doses of 4 mg/kg antibody binding compound may be administered on each of days 1, 2 and 3, followed by subsequent maintenance doses of 6 mg/kg once pet 3 weeks.

An additional regimen involves an initial dose of 4 mg/kg until antibody binding compound, followed by subsequent maintenance doses of 2 mg/kg twice per week, wherein the maintenance doses are separated by 3 days.

Alternatively, the invention may include a cycle of dosing in which delivery of antibody binding compound in 2-3 times per week for 3 weeks. The 3 week cycle is preferably repeated as necessary to achieve suppression of disease symptoms.

The invention further includes a cyclic dosage regimen in which delivery of antibody binding compound is daily for 5 days. According to the invention, the cycle is preferably repeated as necessary to achieve suppression of disease symptoms.

EXAMPLE

Competitive Binding and Off Rates of Antibody Binding Compound BD62

Figures 2A, 2B:
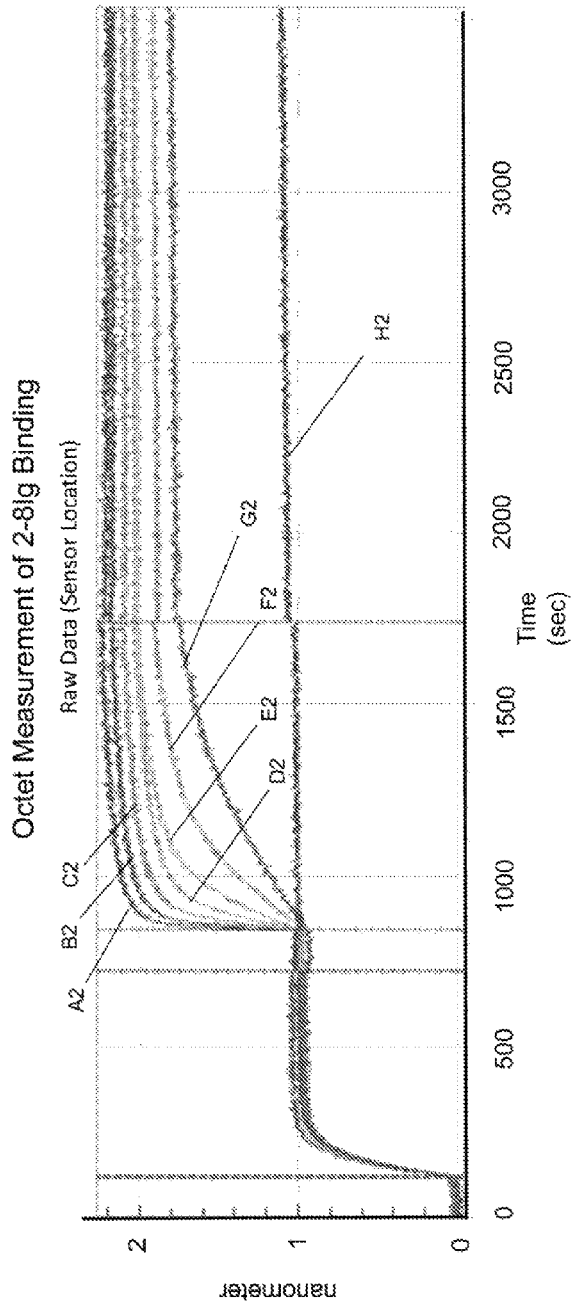
FIG. 2A shows Qctet binding data for invention compound 2-8.
FIG. 2B is a table giving numerical values of binding data for invention compound 2-8.

In this example, phage expressing the following separate compounds (collectively referred to herein as the "BD62" compounds) were assayed for competitive binding to B7H3 and oil-rates from human B7H3: compound 1-1 (heavy and light chains of SEQ ID NO: 13 and SEQ ID NO: 14. respectively; an antibody binding compound comprising the CDRs of Table 2); compound 1-2 (heavy and light chains of SEQ ID NO: 18 and SEQ ID NO: 19, respectively; an antibody binding compound comprising the CDRs of Table 3); compound 1-4 (heavy and light chains of SEQ ID NO: 23 and SEQ ID NO: 24, respectively; an antibody binding compound comprising the CDRs of Table 4); compound 1-5 (heavy and light chains of SEQ ID NO: 28 and SEQ ID NO: 29, respectively; an antibody binding compound comprising the CDRs of Table 5): compound 1-7 (heavy and light chains of SEQ ID NO: 31 and SEQ ID NO: 32, respectively, an antibody binding compound comprising the CDRs of Table 6): and compound 2-5(heavy and light chains of SEQ ID NO: 36 and SEQ ID NO: 37, respectively, an antibody binding compound comprising the CDRs of Table 7). Results are shown in FIGS. 1A-1F. Phage expressing compound 2-8 (heavy and light chains of SEQ ID NO: 7 and SEQ ID NO: 8, respectively; an antibody binding compound comprising the CDRs of Table 8) were assayed for affinity to B7H3 using Octet kinetics analysis. Results of these latter assays are shown in FIGS. 2A-2B.

BD62 competitive ELISA. 1 ug/ml NeutrAvidin (100 ng/well) in PBS was adsorbed to the wells of a 96-well maxisorp plate overnight at 4° C. The next morning the NeutrAvidin solution was removed and the wells were washed once with PBS followed by blocking with Blocking Buffer (PBS+3% BSA) for 60 minutes at room temperature (RT) on a shaking platform. 20 ng of biotinylated B7-H3 (200 ng/ml in Wash Buffer [PBS, 0.5% BSA, 0.05% Tween-20]) was bound to the wells via NeutrAvidin for 90 minutes at RT on a shaking platform. Wash Buffer alone was added to the control wells. The biotinylated B7H3 solution was removed and the wells were washed once with Wash Buffer. Phage was diluted in Wash Buffer to $2\times10^{13}$/ml and $1\times10^{10}$ phage were pre-mixed with B7-H3 (competitor) using 3-fold dilutions from 100 nM to 0.41 nM final concentration. The pre-mix was incubated for 1 minute before adding to the wells and incubated for 90 minutes at RT on a shaking platform. The phage were then removed and the wells were washed 5 times with Wash Buffer. 100 ul of a 1:5000 dilution of anti-M13 HRP conjugated antibody was added to the wells and incubated for 60 minutes at RT on a shaking platform. The secondary antibody was then removed and the wells were washed 5 times with Wash Buffer. Bound phage were detected with 1-Step Ultra TMB and quenched with sulfuric acid. Absorbance at 450 nm was read on a SpectraMax microplate reader. Competitive binding data is shown in the curves of FIG. 1A and values listed in the table of FIG. 1B.

BD62 off-rate ELISA. 1 ug/ml NeutrAvidin (100 ng/well) in PBS was adsorbed to the wells of a 96 well maxisorp plate overnight at 4° C. The next morning the NeutrAvidin solution was removed and the wells were washed once with PBS followed by blocking with Blocking Buffer for 60 minutes at RT on a shaking platform. 20 ng of biotinylated (200 ng/ml in Wash Buffer) was bound to the plate via NeutrAvidin for 90 minutes at RT on a shaking platform. Half of the wells received biotinylated B7-H3, while the other half received Wash Buffer as a non-specific binding control. The biotinylated target solution was removed and the wells were washed once with Wash Buffer. Each phage preparation was diluted in Wash Buffer to $1\times10^{12}$ phage/ml. $1\times10^{11}$ phage were added to the wells and incubated at RT on a shaking platform for 18-22 hours. The phage were then removed and the wells were vaulted 5 times with Wash Buffer. Bound phage was extracted from the wells at time points 0 hours and 48 hours by shaking with 50 mM TCEP in PBS at RT for 15 minutes. Wells that were not extracted at time 0 were left on the shaking platform at RT in 200 ul of Wash Buffer for 48 hours, then extracted with 50 mM TCEP as described. The number of rescued phage from each sample was determined using a SyberGreen amplification reaction with the primers CmF2 (5' TTTCCGGCAGTTTC-TACAC 3') and CmR1 (5' CAGCACCTTGTCGCCTTGC 3') on a Applied Biosystems StepOnePlus Real-time PCR system using a standard curve with phage diluted in PBS at $3 \times 10^8$, $3 \times 10^7$, $3 \times 10^6$, $3 \times 10^5$, $3 \times 10^4$ and 0 phage/well. Off-rate data for 18-hour phage binding is listed in the table of FIG. 1C.

Octet kinetics analysis. An Octet QK (Pall ForteBio, Menlo Park) equipped with ForteBio Streptavidin (SA) Dip and Read Biosensors for kinetics were used to determine binding affinity of each antibody. The Octet analysis was performed at RT using Wash Buffer as the binding buffer. Tips were saturated with 1.8 ug/ml biotinylated B7-H3 for 600 seconds, which resulted in capture of biotinylated target at around 1.0 nm±0.05 nm. Antibody binding compound 8-2 was prepared as 2-fold serial dilution at 100 nM, 50 nM, 25 nM, 12.5 nM, 6.25 nM, 3.12 nM, 1.65 nM in running buffer, plus buffer alone as a negative control (A2, B2, C2, D2, E2, F2, G2 and H2, respectively, in FIG. 2A). Association of each antibody was captured for 900 seconds in wells containing varying concentrations of antibody, followed by dissociation for 1800 seconds into wells containing buffer alone. Compound 2-8 was shown to have a Kd of $2.5 \times 10^{-11}$ of less by this analysis.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

Definitions

Unless otherwise specifically defined herein, terms and symbols of nucleic acid chemistry, biochemistry, genetics, and molecular biology used herein follow those of standard treatises and texts in the field, e.g. Romberg and Baker, DNA Replication, Second Edition (W. H. Freeman, New York, 1992): Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immuology, $6^{th}$ edition (Saunders, 2007).

"Antibody" or "immunoglobulin" means a protein, either natural, or synthetically produced by recombinant or chemical means (but the design of whose antigen binding region is derived from a natural counterpart), which is capable of specifically binding to a particular antigen or antigenic determinant. Antibodies, e.g. IgG antibodies, are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Typically the binding characteristics, e.g. specificity, affinity, and the like, of an antibody, or a binding compound derived from an antibody, are determined by amino acid residues in the $V_H$ and $V_L$ regions, and especially in the six complementary determining regions (CDRs). The constant domains are not involved directly in binding an antibody to an antigen. Depending on the amino acid sequence of the constant domain of their heavy chains, immunoglobulins can be assigned to different classes. There are five major classes of immunoglobulins: IgA, IgD, IgE, IgG, and IgM and several of these can be further divided into subclasses (isotypes), e.g., $IgG_1$, $IgG_2$, $IgG_3$, $IgG_4$, $IgA_1$, and $IgA_2$.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such kilting. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet. Annu. Rev. Immunol. 9:457-92 (1991). To assess ADCC activity of a molecule of interest, an in vitro ADCC assay, such as that described in U.S. Pat. No. 5,500,362 or U.S. Pat. No. 5,821,337 or Presta U.S. Pat. No 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., PNAS (USA) 95:652-656 (1998).

"Antibody fragment", as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Desirably the Kd is $1 \times 10^{-7}$, $1 \times 10^{-8}$, $5 \times 10^{-8}$, $1 \times 10^{-9}$, $3 \times 10^{-9}$, $5 \times 10^{-9}$, or even $1 \times 10^{-10}$ stronger Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Binding compound" means a compound that is capable of specifically binding to a particular target molecule or group of target molecules. "Antibody binding compound" means a binding compound derived from an antibody, such as an antibody fragment, including but not limited to, Fab, Fab', F(ab')$_2$, and Fv fragments, or recombinant films thereof. In some embodiments, an antibody binding compound may comprise a scaffold or framework regions of one antibody and one or more CDR regions of another antibody.

"Complementary-determining region" or "CDR" means a short sequence (from 5 to 18 amino acids) in the variable domains of immunoglobulins. These regions are also referred to herein as hypervariable regions. The CDRs (six of which are present in IgG molecules) are the most variable part of immunoglobulins and contribute to their diversity by making specific contacts with a specific antigen, allowing immunoglobulins to recognize a vast repertoire of antigens with a high affinity, e.g. Beck et al. Nature Reviews Immunology, 10:345-352 (2010). Several numbering schemes, such as the Kabat numbering scheme, provide conventions for describing amino acid locations of CDRs within variable regions of immunoglobulins. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia designations refer to the location of the structural loops (Chothia and Lesk. J. Mol. Biol. 196:901-917 (1987)).

"Cytotoxic agent" as used herein refers to a substance that inhibits or prevents the function of cells and/or causes destruction of cells. The term is intended to include radioactive isotopes (e.g., At211, I113, I125, Y90, Re186, Re188, Sm153, Bi212, P32, and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and or variants thereof, and the various antitumor or anticancer agents disclosed below. Other cytotoxic agents are described below. A tumoricidal agent causes destruction of tumor cells.

"Effector functions" of antibodies refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Fab fragment" contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them.

"Framework" or "FR" residues (or regions) are those variable domain residues other than the CDR or hypervariable region residues as herein defined. A "human consensus framework" is a framework which represents the most commonly occurring amino acid residue in a selection of human immunoglobulin VL or VH framework sequences.

"Fv fragment" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs cooler antigen-binding specificity to the antibody. However, even a single variable domain (or half of an FV comprising only three CDRs specific for an antigen) has the ability to recognize and bind antigen, although at a lower affinity than the entire binding site.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc). typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995): Hurle and Gross, Curr. Op. Biotech. 5:428-433 (1994).

"Isolated" in reference to an antibody or antibody binding compound means such a compound which has been identified and separated and or recovered from a component of its natural environment or from a heterogeneous reaction mixture. Contaminant components of a natural environment or reaction mixture are materials which would interfere with diagnostic or therapeutic uses for the antibody or antibody binding compound, and may include enzymes, hormones, and other proteinaceous or nonproteinaceous solutes. In some embodiments, an antibody or antibody binding compound is purified (1) to greater than 95% by weight of antibody or antibody binding compound as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE; under reducing or nonreducing conditions using Coomassie blue or, preferably, silver stain. When manufactured by recombinant methodologies, an isolated antibody or antibody binding compound may include the antibody or antibody binding compound in situ within recombinant cells since at least one component of the antibody's or antibody binding compound's natural environment will not be present. Ordinarily, an isolated antibody or isolated antibody binding compound is prepared by at least one purification step.

"Monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture or by bacterial, yeast or mammalian expression systems, uncontaminated by other immunoglobulins.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table A below The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in, e.g., WO2007/001851. The ALIGN-2 program should be compiled for use on a UNIX operating system, preferably digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Desirably, two or more amino acid sequences are at least 50%, 60%, 70%, 80%, or 90% identical. More desirably, two or more amino acid sequences are at least 95%, 97%, 98%, 99%, or even 100% identical. Unless specifically stated otherwise, all % amino acid sequence identity values used herein are obtained as described in the immediately preceding paragraph using the ALIGN-2 computer program.

"Phage display" is a technique by which variant polypeptides are displayed as fusion proteins to at least a portion of a coat protein on the surface of phage, e.g., filamentous phage, particles. A utility of phage display lies in the fact that large libraries of randomized protein variants can be rapidly and efficiently selected for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.*, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that selection is on the basis of intrinsic ligand affinity, and phagemid vectors are used, which simplify DNA manipulations. Lowman and Wells, *Methods: A companion to Methods in Enzymology*, 3:205-0216 (1991).

"Phagemid" means a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle implication to generate copies of one strand of the plasmid DMA and package phage particles. The phagemid may form infectious or non-infectious phage particles. This term includes phagemids, which contain a phage coat protein gene or fragment thereof linked to a heterologous polypeptide gene as a gene fusion such that the heterologous polypeptide is displayed on the surface of the phage particle.

"Phage" or "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an Ml3, f1, fd, Pf3 phage or a derivative thereof, or a lambdoid phage, such as lambda, 21, phi80, phi81, 82, 424, 434, etc., or a derivative thereof.

"Polypeptide" refers to a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides, there is no clear-cut distinction between polypeptides and peptides. For convenience, in this disclosure and claims, the term "polypeptide" will be used to refer generally to peptides and polypeptides. The amino acid residues may be natural or synthetic.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenborg and Moore eds., Springer-Verlag, New York, pp. 269-315(1994).

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In some embodiments, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interact ions, and the like, dominate the interaction of the molecules.

"Therapeutically effective amount" means an amount having anti-proliferative effect on a cancer. In some embodiments, a therapeutically effective amount is an amount that induces apoptotic activity, or is capable of inducing cell death, particularly death of benign or malignant tumor cells. Such efficacy can be measured in conventional ways, depending on the condition to be treated. For cancer therapy, such efficacy can, for example, be measured by assessing the time to disease progression, or determining the response rates. Therapeutically effective amount also refers to a target serum concentration of an antibody binding compound of the invention, such as a trough serum concentration, that has been shown to be effective in suppressing disease symptoms when maintained for a period of time.

"Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the βsheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. "Variable domain residue numbering as in Kabat" or "amino acid position numbering as in Kabat."and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52*a* according to Kabat) after residue 52 of H2 and inserted residues (e.g. residues 82*a*, 82*b*, and 82*c*, etc according to Kabat) after heavy chain FR residue 82. The Kabat numbering of residues may be determined for a given antibody by alignment at regions of homology of the sequence of the antibody with a "standard" Kabat numbered sequence "Vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referral to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

What is claimed is:

1. An isolated antibody binding compound specific for the human B7H3 comprising heavy chain and light chain complementary determining regions (CDRs) defined by the following amino acid sequences:
   heavy chain CDR1: N-Y-D-I-N (SEQ ID NO: 1);
   heavy chain CDR2: W-I-F-P-G-D-G-S-T-Q-Y-N-G-K-F-K-G (SEQ ID NO: 9);
   heavy chain CDR3: Q-T-T-G-T-W-F-A-Y (SEQ ID NO: 10);
   light chain CDR1: R-A-S-Q-S-I-S-P-Y-L-H (SEQ ID NO: 11);
   light chain CDR2: Y-A-S-Q-S-W-S (SEQ ID NO: 12); and
   light chain CDR3: Q-N-G-H-S-F-P-L-T (SEQ ID NO: 6).

2. The isolated antibody binding compound of claim 1 wherein said isolated antibody binding compound has an affinity for human B7H3 that is characterized by an equilibrium binding constant of 100 nM or less.

3. An isolated antibody binding compound specific for the human B7H3 comprising heavy chain and light chain complementary determining regions (CDRs) defined by the following amino acid sequences:
   heavy chain CDR1: N-Y-D-I-N (SEQ ID NO: 1);
   heavy chain CDR2: W-I-F-P-G-D-G-S-T-Q-Y-N-E-T-F-K-G (SEQ ID NO: 15);
   heavy chain CDR3: Q-T-T-G-T-W-F-A-Y (SEQ ID NO: 10);
   light chain CDR1: R-A-S-Q-S-I-S-K-Y-L-H (SEQ ID NO: 16);
   light chain CDR2: Y-A-N-Q-S-I-R (SEQ ID NO: 17); and
   light chain CDR3: Q-N-G-H-S-F-P-L-T (SEQ ID NO: 6).

4. The isolated antibody compound of claim 3 wherein said isolated antibody binding compound has an affinity for human B7H3 that is characterized by an equilibrium binding constant of 100 nM or less.

5. An isolated antibody binding compound specific for the human B7H3 comprising heavy chain and light chain complementary determining regions (CDRs) defined by the following amino acid sequences:
   heavy chain CDR1: N-Y-D-I-N (SEQ ID NO: 1);
   heavy chain CDR2: W-I-F-P-G-D-G-S-T-Q-Y-N-P-K-F-K-G (SEQ ID NO: 20);
   heavy chain CDR3: Q-T-T-G-T-W-F-A-Y (SEQ ID NO: 10);
   light chain CDR1: R-A-S-Q-S-I-S-T-Y-L-H (SEQ ID NO: 21);

light chain CDR2: E-A-S-Q-S-I-S (SEQ ID NO: 22); and
light chain CDR3: Q-N-G-H-S-F-P-L-T (SEQ ID NO: 6).

6. The isolated antibody binding compound of claim 5 wherein said isolated antibody binding compound has an affinity for human B7H3 that is characterized by an equilibrium binding constant of 100 μM or less.

7. An isolated antibody binding compound specific for the human B7H3 comprising heavy chain and light chain complementary determining regions (CDRs) defined by the following amino acid sequences:
heavy chain CDR1: N-Y-D-I-N (SEQ ID NO: 1);
heavy chain CDR2: W-I-F-P-G-D-G-S-T-Q-Y-N-E-K-F-K-G (SEQ ID NO: 25);
heavy chain CDR3: Q-T-T-G-T-W-F-A-Y (SEQ ID NO: 10);
light chain CDR1: R-A-S-Q-S-I-S-H-Y-L-H (SEQ ID NO: 26);
light chain CDR2: Y-A-S-Q-S-L-S (SEQ ID NO: 27); and
light chain CDR3: Q-N-G-H-S-F-P-L-T (SEQ ID NO: 6).

8. The isolated antibody binding compound of claim 7 wherein said isolated antibody binding compound has an affinity for human B7H3 that is characterized by an equilibrium binding constant of 100 nM or less.

9. An isolated antibody binding compound specific for the human B7H3 comprising heavy chain and light chain complementary determining regions (CDRs) defined by the following amino acid sequences:
heavy chain CDR1: N-Y-D-I-N (SEQ ID NO: 1);
heavy chain CDR2: W-I-F-P-G-D-G-S-T-Q-Y-N-E-K-F-K-G (SEQ ID NO: 25);
heavy chain CDR3: Q-T-T-G-T-W-F-A-Y (SEQ ID NO: 10);
light chain CDR1: R-A-S-Q-S-I-S-P-Y-L-H (SEQ ID NO: 11);
light chain CDR2: H-A-S-Q-S-I-S (SEQ ID NO: 30); and
light chain CDR3: Q-N-G-H-S-F-P-L-T (SEQ ID NO: 6).

10. The isolated antibody binding compound of claim 9 wherein said isolated antibody binding compound has an affinity for human B7H3 that is characterized by an equilibrium binding constant of 100 nM or less.

11. An isolated antibody binding compound specific for the human B7H3 comprising heavy chain and light chain complementary determining regions (CDRs) defined by the following amino acid sequences:
heavy chain CDR1: N-Y-D-I-N (SEQ ID NO: 1);
heavy chain CDR2: W-I-F-P-G-D-G-S-T-Q-Y-N-E-K-F-K-G (SEQ ID NO: 25);
heavy chain CDR3: Q-T-T-S-T-W-F-A-Y (SEQ ID NO: 33);
light chain CDR1: R-A-S-Q-I-I-S-D-Y-L-H (SEQ ID NO: 34);
light chain CDR2: Y-A-S-Q-L-I-S (SEQ ID NO: 35); and
light chain CDR3: Q-N-G-H-S-F-P-L-T (SEQ ID NO: 6).

12. The isolated antibody binding compound of claim 11 wherein said isolated antibody binding compound has an affinity for human B7H3 that is characterized by an equilibrium binding constant of 100 nM or less.

13. An isolated antibody binding compound specific for the human B7H3 comprising heavy chain and light chain complementary determining regions (CDRs) defined by the following amino acid sequences:
heavy chain CDR1: N-Y-D-I-N (SEQ ID NO: 1);
heavy chain CDR2: W-I-F-P-G-D-G-S-T-Q-Y-N-E-K-F-K-G (SEQ ID NO: 25);
heavy chain CDR3: Q-T-T-G-T-W-F-A-Y (SEQ ID NO: 10);
light chain CDR1: R-A-S-Q-S-I-S-E-Y-L-H (SEQ ID NO: 38);
light chain CDR2: H-A-S-Q-S-I-S (SEQ ID NO: 30); and
light chain CDR3: Q-N-G-H-S-F-P-L-T (SEQ ID NO: 6).

14. The isolated antibody binding compound of claim 13 wherein said isolated antibody binding compound has an affinity for human B7H3 that is characterized by an equilibrium binding constant of 100 μM or less.

* * * * *

SEQUENCE LISTING

<160> NUMBER OF SEQ ID NOS: 38

<210> SEQ ID NO 1
<211> LENGTH: 5
<212> TYPE: PRT
<213> ORGANISM: Homo sapiens

<400> SEQUENCE: 1

Asn Tyr Asp Ile Asn
1               5

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Xaa is E, G or P
<220> FEATURE:
<221> NAME/KEY: MISC_FEATURE
<222> LOCATION: (14)..(14)
<223> OTHER INFORMATION: Xaa is K or T

<400> SEQUENCE: 2

Trp Ile Phe Pro Gly Asp Gly Ser Thr Gln Tyr Asn Xaa Xaa Phe Lys
1               5                   10                  15

Gly

<210> SEQ ID NO 3
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is G, S, M or N.

<400> SEQUENCE: 3

Gln Thr Thr Xaa Thr Trp Phe Ala Tyr
1               5

<210> SEQ ID NO 4
<211> LENGTH: 11
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is S or I
<220> FEATURE:
<221> NAME/KEY: MISC_FEATURE
<222> LOCATION: (8)..(8)
<223> OTHER INFORMATION: Xaa is E, P, V, H, T, K or D.
<220> FEATURE:
<221> NAME/KEY: MISC_FEATURE
<222> LOCATION: (9)..(9)
<223> OTHER INFORMATION: Xaa is Y or W.

<400> SEQUENCE: 4

Arg Ala Ser Gln Xaa Ile Ser Xaa Xaa Leu His
1               5                   10

<210> SEQ ID NO 5
<211> LENGTH: 7
<212> TYPE: PRT
<213> ORGANISM: Homo sapiens
<220> FEATURE:
<221> NAME/KEY: MISC_FEATURE

```
<222> LOCATION: (1)..(1)
<223> OTHER INFORMATION: Xaa is H, Y, N or E.
<220> FEATURE:
<221> NAME/KEY: MISC_FEATURE
<222> LOCATION: (3)..(3)
<223> OTHER INFORMATION: Xaa is S or N.
<220> FEATURE:
<221> NAME/KEY: MISC_FEATURE
<222> LOCATION: (5)..(5)
<223> OTHER INFORMATION: Xaa is S or L.
<220> FEATURE:
<221> NAME/KEY: MISC_FEATURE
<222> LOCATION: (6)..(6)
<223> OTHER INFORMATION: Xaa is I, W or L.
<220> FEATURE:
<221> NAME/KEY: MISC_FEATURE
<222> LOCATION: (7)..(7)
<223> OTHER INFORMATION: Xaa is S or R.

<400> SEQUENCE: 5

Xaa Ala Xaa Gln Xaa Xaa Xaa
1               5

<210> SEQ ID NO 6
<211> LENGTH: 9
<212> TYPE: PRT
<213> ORGANISM: Homo sapiens

<400> SEQUENCE: 6

Gln Asn Gly His Ser Phe Pro Leu Thr
1               5

<210> SEQ ID NO 7
<211> LENGTH: 448
<212> TYPE: PRT
<213> ORGANISM: Homo sapiens

<400> SEQUENCE: 7

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Asp Ile Asn Trp Val Arg Gln Ala Pro Gly Gln Gly Leu Glu Trp Ile
            35                  40                  45

Gly Trp Ile Phe Pro Gly Asp Gly Ser Thr Gln Tyr Asn Glu Lys Phe
        50                  55                  60

Lys Gly Arg Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 8
<211> LENGTH: 214
<212> TYPE: PRT
<213> ORGANISM: Homo sapiens

<400> SEQUENCE: 8

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Glu Tyr
            20                  25                  30

Leu His Trp Tyr Gln Gln Lys Pro Gly Gln Ala Pro Arg Leu Leu Ile
        35                  40                  45

Lys His Ala Ser Gln Ser Ile Ser Gly Ile Pro Ala Arg Phe Ser Gly
    50                  55                  60

Ser Gly Ser Gly Ser Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 17
<212> TYPE: PRT
<213> ORGANISM: Homo sapiens

<400> SEQUENCE: 9

Trp Ile Phe Pro Gly Asp Gly Ser Thr Gln Tyr Asn Gly Lys Phe Lys
1               5                   10                  15

Gly

<210> SEQ ID NO 10
<211> LENGTH: 9
<212> TYPE: PRT
<213> ORGANISM: Homo sapiens

<400> SEQUENCE: 10

Gln Thr Thr Gly Thr Trp Phe Ala Tyr
1               5

<210> SEQ ID NO 11
<211> LENGTH: 11
<212> TYPE: PRT
<213> ORGANISM: Homo sapiens

<400> SEQUENCE: 11

Arg Ala Ser Gln Ser Ile Ser Pro Tyr Leu His
1               5                   10

<210> SEQ ID NO 12
<211> LENGTH: 7
<212> TYPE: PRT
<213> ORGANISM: Homo sapiens

<400> SEQUENCE: 12

Tyr Ala Ser Gln Ser Trp Ser
1               5

<210> SEQ ID NO 13
<211> LENGTH: 448
<212> TYPE: PRT
<213> ORGANISM: Homo sapiens

<400> SEQUENCE: 13

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

-continued

```
Asp Ile Asn Trp Val Arg Gln Ala Pro Gly Gln Gly Leu Glu Trp Ile
     35                  40                  45

Gly Trp Ile Phe Pro Gly Asp Gly Ser Thr Gln Tyr Asn Gly Lys Phe
 50                  55                  60

Lys Gly Arg Ala Thr Leu Thr Thr Asp Thr Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Gln Thr Thr Gly Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 14
<211> LENGTH: 214
<212> TYPE: PRT
<213> ORGANISM: Homo sapiens

<400> SEQUENCE: 14

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Pro Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Trp Ser Gly Ile Pro Ala Arg Phe Ser Gly
    50                  55                  60

Ser Gly Ser Gly Ser Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 17
<212> TYPE: PRT
<213> ORGANISM: Homo sapiens

<400> SEQUENCE: 15

Trp Ile Phe Pro Gly Asp Gly Ser Thr Gln Tyr Asn Glu Thr Phe Lys
1               5                   10                  15

Gly

<210> SEQ ID NO 16
<211> LENGTH: 11
<212> TYPE: PRT
<213> ORGANISM: Homo sapiens

<400> SEQUENCE: 16

Arg Ala Ser Gln Ser Ile Ser Lys Tyr Leu His
1               5                   10

<210> SEQ ID NO 17
<211> LENGTH: 7
<212> TYPE: PRT
<213> ORGANISM: Homo sapiens
```

```
<400> SEQUENCE: 17

Tyr Ala Asn Gln Ser Ile Arg
1               5

<210> SEQ ID NO 18
<211> LENGTH: 448
<212> TYPE: PRT
<213> ORGANISM: Homo sapiens

<400> SEQUENCE: 18

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Phe Pro Gly Asp Gly Ser Thr Gln Tyr Asn Glu Thr Phe
    50                  55                  60

Lys Gly Arg Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445
```

<210> SEQ ID NO 19
<211> LENGTH: 214
<212> TYPE: PRT
<213> ORGANISM: Homo sapiens

<400> SEQUENCE: 19

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Lys Tyr
            20                  25                  30

Leu His Trp Tyr Gln Gln Lys Pro Gly Gln Ala Pro Arg Leu Leu Ile
        35                  40                  45

Lys Tyr Ala Asn Gln Ser Ile Arg Gly Ile Pro Ala Arg Phe Ser Gly
    50                  55                  60

Ser Gly Ser Gly Ser Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 20
<211> LENGTH: 17
<212> TYPE: PRT
<213> ORGANISM: Homo sapiens

<400> SEQUENCE: 20

```
Trp Ile Phe Pro Gly Asp Gly Ser Thr Gln Tyr Asn Pro Lys Phe Lys
1               5                   10                  15
```

Gly

<210> SEQ ID NO 21
<211> LENGTH: 11
<212> TYPE: PRT
<213> ORGANISM: Homo sapiens

<400> SEQUENCE: 21

Arg Ala Ser Gln Ser Ile Ser Thr Tyr Leu His
1               5                   10

<210> SEQ ID NO 22
<211> LENGTH: 7
<212> TYPE: PRT
<213> ORGANISM: Homo sapiens

<400> SEQUENCE: 22

Glu Ala Ser Gln Ser Ile Ser
1               5

<210> SEQ ID NO 23
<211> LENGTH: 448
<212> TYPE: PRT
<213> ORGANISM: Homo sapiens

<400> SEQUENCE: 23

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Phe Pro Gly Asp Gly Ser Thr Gln Tyr Asn Pro Lys Phe
    50                  55                  60

Lys Gly Arg Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 24
<211> LENGTH: 214
<212> TYPE: PRT
<213> ORGANISM: Homo sapiens

<400> SEQUENCE: 24

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Tyr
            20                  25                  30

Leu His Trp Tyr Gln Gln Lys Pro Gly Gln Ala Pro Arg Leu Leu Ile
        35                  40                  45

Lys Glu Ala Ser Gln Ser Ile Ser Gly Ile Pro Ala Arg Phe Ser Gly
    50                  55                  60

Ser Gly Ser Gly Ser Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr

```
                180              185                190
Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 25
<211> LENGTH: 17
<212> TYPE: PRT
<213> ORGANISM: Homo sapiens

<400> SEQUENCE: 25

```
Trp Ile Phe Pro Gly Asp Gly Ser Thr Gln Tyr Asn Glu Lys Phe Lys
1               5                   10                  15

Gly
```

<210> SEQ ID NO 26
<211> LENGTH: 11
<212> TYPE: PRT
<213> ORGANISM: Homo sapiens

<400> SEQUENCE: 26

```
Arg Ala Ser Gln Ser Ile Ser His Tyr Leu His
1               5                   10
```

<210> SEQ ID NO 27
<211> LENGTH: 7
<212> TYPE: PRT
<213> ORGANISM: Homo sapiens

<400> SEQUENCE: 27

```
Tyr Ala Ser Gln Ser Leu Ser
1               5
```

<210> SEQ ID NO 28
<211> LENGTH: 448
<212> TYPE: PRT
<213> ORGANISM: Homo sapiens

<400> SEQUENCE: 28

```
Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Arg Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
```

```
                145                 150                 155                 160
        Ser Gly Ala Leu Thr Ser Gly Val His Thr Phe Pro Ala Val Leu Gln
                        165                 170                 175
        Ser Ser Gly Leu Tyr Ser Leu Ser Ser Val Thr Val Pro Ser Ser
                        180                 185                 190
        Ser Leu Gly Thr Gln Thr Tyr Ile Cys Asn Val Asn His Lys Pro Ser
                        195                 200                 205
        Asn Thr Lys Val Asp Lys Lys Val Glu Pro Lys Ser Cys Asp Lys Thr
                        210                 215                 220
        His Thr Cys Pro Pro Cys Pro Ala Pro Glu Leu Leu Gly Gly Pro Ser
        225                 230                 235                 240
        Val Phe Leu Phe Pro Pro Lys Pro Lys Asp Thr Leu Met Ile Ser Arg
                        245                 250                 255
        Thr Pro Glu Val Thr Cys Val Val Val Asp Val Ser His Glu Asp Pro
                        260                 265                 270
        Glu Val Lys Phe Asn Trp Tyr Val Asp Gly Val Glu Val His Asn Ala
                        275                 280                 285
        Lys Thr Lys Pro Arg Glu Glu Gln Tyr Asn Ser Thr Tyr Arg Val Val
                        290                 295                 300
        Ser Val Leu Thr Val Leu His Gln Asp Trp Leu Asn Gly Lys Glu Tyr
        305                 310                 315                 320
        Lys Cys Lys Val Ser Asn Lys Ala Leu Pro Ala Pro Ile Glu Lys Thr
                        325                 330                 335
        Ile Ser Lys Ala Lys Gly Gln Pro Arg Glu Pro Gln Val Tyr Thr Leu
                        340                 345                 350
        Pro Pro Ser Arg Asp Glu Leu Thr Lys Asn Gln Val Ser Leu Thr Cys
                        355                 360                 365
        Leu Val Lys Gly Phe Tyr Pro Ser Asp Ile Ala Val Glu Trp Glu Ser
                        370                 375                 380
        Asn Gly Gln Pro Glu Asn Asn Tyr Lys Thr Thr Pro Pro Val Leu Asp
        385                 390                 395                 400
        Ser Asp Gly Ser Phe Phe Leu Tyr Ser Lys Leu Thr Val Asp Lys Ser
                        405                 410                 415
        Arg Trp Gln Gln Gly Asn Val Phe Ser Cys Ser Val Met His Glu Ala
                        420                 425                 430
        Leu His Asn His Tyr Thr Gln Lys Ser Leu Ser Leu Ser Pro Gly Lys
                        435                 440                 445

<210> SEQ ID NO 29
<211> LENGTH: 214
<212> TYPE: PRT
<213> ORGANISM: Homo sapiens

<400> SEQUENCE: 29

Asp Ile Val Leu Thr Gln Ser Pro Ala Thr Leu Ser Leu Ser Pro Gly
        1               5                   10                  15
        Glu Arg Ala Thr Leu Ser Cys Arg Ala Ser Gln Ser Ile Ser His Tyr
                        20                  25                  30
        Leu His Trp Tyr Gln Gln Lys Pro Gly Gln Ala Pro Arg Leu Leu Ile
                        35                  40                  45
        Lys Tyr Ala Ser Gln Ser Leu Ser Gly Ile Pro Ala Arg Phe Ser Gly
                        50                  55                  60
        Ser Gly Ser Gly Ser Asp Phe Thr Leu Thr Ile Ser Ser Leu Glu Pro
        65                  70                  75                  80
```

```
Glu Asp Phe Ala Val Tyr Tyr Cys Gln Asn Gly His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 7
<212> TYPE: PRT
<213> ORGANISM: Homo sapiens

<400> SEQUENCE: 30

His Ala Ser Gln Ser Ile Ser
1               5

<210> SEQ ID NO 31
<211> LENGTH: 448
<212> TYPE: PRT
<213> ORGANISM: Homo sapiens

<400> SEQUENCE: 31

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Tyr Thr Asn Tyr
            20                  25                  30

Asp Ile Asn Trp Val Arg Gln Ala Pro Gly Gln Gly Leu Glu Trp Ile
        35                  40                  45

Gly Trp Ile Phe Pro Gly Asp Gly Ser Thr Gln Tyr Asn Glu Lys Phe
    50                  55                  60

Lys Gly Arg Ala Thr Leu Thr Thr Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gln Thr Thr Gly Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 32
<211> LENGTH: 214
<212> TYPE: PRT
<213> ORGANISM: Homo sapiens

<400> SEQUENCE: 32

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Pro Tyr
            20                  25                  30

Leu His Trp Tyr Gln Gln Lys Pro Gly Gln Ala Pro Arg Leu Leu Ile
        35                  40                  45

Lys His Ala Ser Gln Ser Ile Ser Gly Ile Pro Ala Arg Phe Ser Gly
    50                  55                  60

Ser Gly Ser Gly Ser Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gly Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 33
<211> LENGTH: 9
<212> TYPE: PRT
<213> ORGANISM: Homo sapiens

<400> SEQUENCE: 33

```
Gln Thr Thr Ser Thr Trp Phe Ala Tyr
1               5
```

<210> SEQ ID NO 34
<211> LENGTH: 11
<212> TYPE: PRT
<213> ORGANISM: Homo sapiens

<400> SEQUENCE: 34

```
Arg Ala Ser Gln Ile Ile Ser Asp Tyr Leu His
1               5                   10
```

<210> SEQ ID NO 35
<211> LENGTH: 7
<212> TYPE: PRT
<213> ORGANISM: Homo sapiens

<400> SEQUENCE: 35

```
Tyr Ala Ser Gln Leu Ile Ser
1               5
```

<210> SEQ ID NO 36
<211> LENGTH: 448
<212> TYPE: PRT
<213> ORGANISM: Homo sapiens

<400> SEQUENCE: 36

```
Gln Val Gln Leu Gln Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Asp Ile Asn Trp Val Arg Gln Ala Pro Gly Gln Gly Leu Glu Trp Ile
        35                  40                  45
Gly Trp Ile Phe Pro Gly Asp Gly Ser Thr Gln Tyr Asn Glu Lys Phe
    50                  55                  60
Lys Gly Arg Ala Thr Leu Thr Thr Asp Thr Ser Thr Ser Thr Ala Tyr
65                  70                  75                  80
Met Glu Leu Ser Ser Leu Arg Ser Glu Asp Thr Ala Val Tyr Phe Cys
```

```
            85                  90                  95
Ala Arg Gln Thr Thr Ser Thr Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 37
<211> LENGTH: 214
<212> TYPE: PRT
<213> ORGANISM: Homo sapiens

<400> SEQUENCE: 37

Asp Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ile Ile Ser Asp Tyr
            20                  25                  30
Leu His Trp Tyr Gln Gln Lys Pro Gly Gln Ala Pro Arg Leu Leu Ile
            35                  40                  45
Lys Tyr Ala Ser Gln Leu Ile Ser Gly Ile Pro Ala Arg Phe Ser Gly
 50                      55                  60
Ser Gly Ser Gly Ser Asp Phe Thr Leu Thr Ile Ser Ser Leu Glu Pro
 65                  70                      75                  80
Glu Asp Phe Ala Val Tyr Tyr Cys Gln Asn Gly His Ser Phe Pro Leu
                 85                      90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
                195                 200                 205
Phe Asn Arg Gly Glu Cys
    210

<210> SEQ ID NO 38
<211> LENGTH: 11
<212> TYPE: PRT
<213> ORGANISM: Homo sapiens

<400> SEQUENCE: 38

Arg Ala Ser Gln Ser Ile Ser Glu Tyr Leu His
1               5                   10
```